United States Patent
Chouthaiwale et al.

(10) Patent No.: US 9,346,780 B2
(45) Date of Patent: May 24, 2016

(54) PROCESS FOR PRODUCING DIHYDRO-2H-PYRAN DERIVATIVES

(71) Applicant: OKINAWA INSTITUTE OF SCIENCE AND TECHNOLOGY SCHOOL CORPORATION, Okinawa (JP)

(72) Inventors: Pandurang V. Chouthaiwale, Okinawa (JP); Fujie Tanaka, Okinawa (JP)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 0 days.

(21) Appl. No.: 14/431,945

(22) PCT Filed: Oct. 10, 2013

(86) PCT No.: PCT/JP2013/078249
§ 371 (c)(1),
(2) Date: Mar. 27, 2015

(87) PCT Pub. No.: WO2014/058078
PCT Pub. Date: Apr. 17, 2014

(65) Prior Publication Data
US 2015/0246896 A1  Sep. 3, 2015

Related U.S. Application Data

(60) Provisional application No. 61/713,198, filed on Oct. 12, 2012.

(51) Int. Cl.
| | |
|---|---|
| A61K 31/35 | (2006.01) |
| C07D 309/16 | (2006.01) |
| C07D 309/28 | (2006.01) |
| C07D 309/30 | (2006.01) |
| C07D 317/30 | (2006.01) |
| C07C 201/14 | (2006.01) |
| C07D 407/04 | (2006.01) |
| C07D 241/44 | (2006.01) |
| C07D 243/02 | (2006.01) |
| C07D 307/54 | (2006.01) |
| C07C 205/55 | (2006.01) |

(52) U.S. Cl.
CPC ............ *C07D 309/28* (2013.01); *C07C 201/14* (2013.01); *C07C 205/55* (2013.01); *C07D 241/44* (2013.01); *C07D 243/02* (2013.01); *C07D 307/54* (2013.01); *C07D 309/30* (2013.01); *C07D 317/30* (2013.01); *C07D 407/04* (2013.01); *C07C 2101/14* (2013.01)

(58) Field of Classification Search
CPC .......................... A61K 31/35; C07D 309/16
USPC ..................... 549/356, 420; 514/451, 460
See application file for complete search history.

(56) References Cited

U.S. PATENT DOCUMENTS

2004/0059138 A1   3/2004   Schreiber et al.

FOREIGN PATENT DOCUMENTS

| EP | 0219091 A2 | 4/1987 |
| EP | 0254078 A1 | 1/1988 |
| JP | 62-93285 A | 4/1987 |
| JP | 63-93776 A | 4/1988 |

OTHER PUBLICATIONS

Gademann et al., "Highly Enantioselective Inverse-Electron-Demand Hetero-Diels-Alder Reactions of α, β-Unsaturated Aldehydes", Angew. Chem. Int. Ed., 2002, vol. 41, No. 16, pp. 3059-3061.

Dong et al., "One-Pot Formation of Chiral Polysubstituted 3,4-Dihydropyrans via a Novel Organocatalytic Domino Sequence Involving Alkynal Self-Condensation", Org. Lett., 2013, vol. 15, No. 1, pp. 204-207 (Mentioned in paragraph Nos. 3-4 of the as-filed specification.).

Tian et al., "Inhibitor Ionization as a Determinant of Binding to 3-Dehydroquinate Synthase", J. Org. Chem., 1996, vol. 61, No. 21, pp. 7373-7381.

Dini et al., "New Polyphenol Derivative in Ipomoea batatas Tubers and Its Antioxidant Activity", J. Agric. Food Chem., 2006, vol. 54, No. 23, pp. 8733-8737.

Barton et al., "The Structure of Daucic Acid", J. Chem. Soc. Perkin Trans 1, 1975, No. 20, pp. 2069-2076.

(Continued)

*Primary Examiner* — Golam M M Shameem

(74) *Attorney, Agent, or Firm* — Chen Yoshimura LLP

(57) ABSTRACT

Disclosed is a process for preparing dihydro-2H-pyran derivatives of formula I: wherein $R^1$ and $R^2$ are defined herein. The process of the invention provides the compound of formula I in concise cascade reactions and in one pot. The compound of formulae I prepared by the process of the invention and its further transformed derivatives are useful for making pharmaceutical composition for the treatment of proliferative diseases.

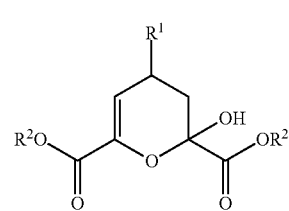

I

4 Claims, No Drawings

(56) References Cited

OTHER PUBLICATIONS

Pandurang et al., "Reactions of pyruvates: organocatalytic synthesis of functionalized dihydropyrans in one pot and further transformations to functionalized carbocycles and heterocycles", Chem. Commun., Dec. 7, 2014, vol. 50, No. 94, pp. 14881-14884.

International Search Report (ISR) issued in PCT/JP2013/078249 mailed in Jan. 2014.

Written Opinion (PCT/ISA/237) issued in PCT/JP2013/078249 mailed in Jan. 2014.

European Search Report dated Jan. 7, 2016, in a counterpart European patent application No. 13845790.8.

PROCESS FOR PRODUCING DIHYDRO-2H-PYRAN DERIVATIVES

TECHNICAL FIELD

The present invention relates to one-pot amino acid-catalyzed construction of functionalized dihydro-2H-pyran derivatives via aldol condensation-Michael addition-cyclization cascade reactions starting from pyruvates (or 2-oxopropanoates) and aldehydes (Scheme 1). This invention provides a new system to access the dihydro-2H-pyran derivatives as new compounds.

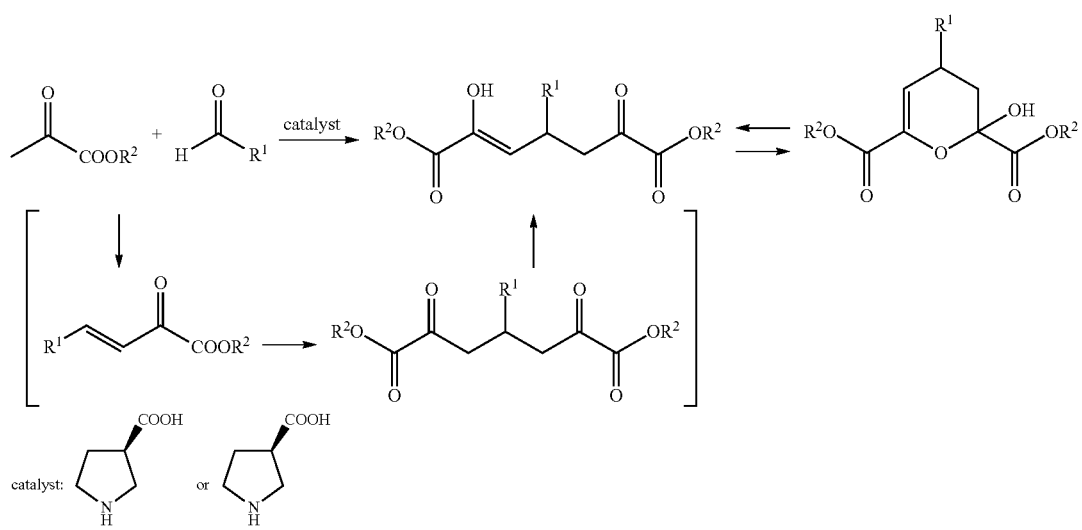

Scheme 1

BACKGROUND ART

Dihydropyran is an important core structure as often found in bioactive natural products, pharmaceuticals and intermediates thereof. These dihydropyran compounds can be obtained by hetero Diels-Alder reaction. For example, the hetero Diels-Alder reaction with inverse electron demand, catalyzed by $Cr^{III}$-Schiff base complexes is reported to synthesize 3,4-dihydro-2H-pyran compounds from vinyl ether compounds and α,β-unsaturated aldehydes (see Non-Patent Literature 1). One-pot formation of chiral polysubstituted 3,4-dihydropyrans via a novel organocatalytic domino sequence involving alkynal self-condensation is also reported (see Non-Patent Literature 2).

PRIOR ART LITERATURES

Non-Patent Documents

[Non-Patent Literature 1] Gademann K, Chavez D E, and Jacobsen E N, Angew. Chem. Int. Ed., 2002, vol. 41, No. 16, p 3059-3061

[Non-Patent Literature 2] Dong L J, Fan T T, and Sun J, Org. Lett. 2013, vol. 15, No. 1, p 204-207

SUMMARY OF THE INVENTION

However, there is still a need for synthetic methods that allow access to diverse functionalized dihydropyrans in concise route under mild conditions, which are important in the search for new biofunctional molecules and their leads. Thus, it is an object of the present invention to provide a process for concise cascade reactions to generate functionalized dihydropyran derivatives in one pot.

The present inventors hypothesized that pyruvates can act as nucleophiles and electrophiles, and these features could be harnessed through use of appropriate catalysis and conditions to provide dihydropyran derivatives via an aldol condensation-Michael addition-cyclization cascade reaction in one pot, which have led to the completion of the present invention.

In one aspect, the present invention relates to a process for preparing dihydro-2H-pyran derivatives of formula I:

I wherein $R^1$ is alkyl, cycloalkyl, aryl or heteroaryl, which is optionally substituted with one or more substituent selected from the group consisting of alkyl, alkenyl, alkynyl, alkoxy, nitro, cyano, halogen, hydroxyl, mono- or polyhalo alkyl, mono- or polyhalo alkoxy and phenyl; and $R^2$ is alkyl or benzyl;

which process comprises reacting aldehydes of the following formula:

$R^1$—CHO wherein $R^1$ is as defined in the above;

with pyruvates of the following formula:

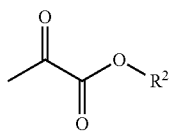

wherein R² is as defined in the above;
in the presence of catalytic amount of β-proline.

In another aspect, the present invention relates to a compound of formula II:

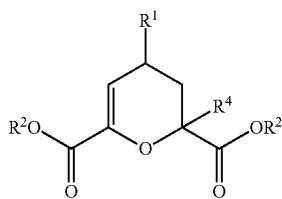

wherein R¹ and R² are as defined above, and R⁴ is hydroxyl or halogen;
or racemate, enantiomer, diastereomer, mixture thereof, or pharmaceutically acceptable salt thereof. The present invention also relates to further transformation derivatives from the compounds of formula I and II, or their pharmaceutically acceptable salts, medicaments containing the said compounds or their pharmaceutically acceptable salts, to the use of the said compounds or their pharmaceutically acceptable salts for the treatment or prophylaxis of illnesses, especially in the treatment or prophylaxis of proliferative diseases.

Further aspects of the invention are described below.

DETAILED DESCRIPTION OF THE INVENTION

In the present disclosure, certain details are set forth such as specific quantities, concentrations, sizes, etc. so as to provide a through understanding of the various embodiments disclosed herein. However, it will be apparent to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of skill in the art, the following definitions are nevertheless put forth to aid in the understanding of the present disclosure. It should be understood, however, that when not explicitly defined, terms should be interpreted as adopting a meaning present accepted by those of skill in the art.

The term "halogen" and "halo" are used interchangeably herein and denote fluoro, chloro, bromo, or iodo. Particular halogens are chloro and fluoro.

The term "alkyl" denotes a monovalent linear or branched saturated hydrocarbon group of 1 to 24 carbon atoms, in particular of 1 to 18 carbon atoms, more particular of 1 to 12 carbon atoms, for example, methyl, ethyl, n-propyl, isopropyl, n-butyl, iso-butyl, sec-butyl, and tert-butyl. The term "lower alkyl" intends an alkyl group of one to six carbon atoms, and includes, for example, methyl, ethyl, n-propyl and isopropyl. More particular alkyl group is methyl.

The term "cycloalkyl", alone or in combination with other groups, denotes a monovalent saturated monocyclic or bicyclic hydrocarbon group of 3 to 18 ring carbon atoms, particularly a monovalent saturated monocyclic hydrocarbon group of 3 to 8 ring carbon atoms. Examples for monocyclic cycloalkyl are cyclopropyl, cyclobutanyl, cyclopentyl, cyclohexyl or cycloheptyl.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy, n-propoxy and isopropoxy.

The term "halo-alkyl" denotes an alkyl group wherein at least one of the hydrogen atoms of the alkyl group has been replaced by same or different halogen atoms. Examples of haloalkyl include fluoromethyl, difluoromethyl, trifluoromethyl, 1,1,1-trifluoroethyl, 1,1,1-trifluoropropyl and pentafluoroethyl. Particular haloalkyl group is trifluoromethyl.

The term "halo-alkoxy" denotes an alkoxy group wherein at least one of the hydrogen atoms of the alkoxy group has been replaced by same or different halogen atoms. Examples of haloalkoxy include fluoromethoxy, difluoromethoxy, trifluoromethoxy, 1,1,1-trifluoroethoxy, 1,1,1-trifluoropropoxy, and pentafluoroethoxy. Particular haloalkoxy groups are trifluoromethoxy and 1,1,1-trifluoroethoxy.

The term "alkenyl" denotes a branched, unbranched or cyclic (e.g. in the case of C5 and C6) hydrocarbon group of 2 to 18, or 2 to 12 in some embodiments, carbon atoms containing at least one double bond, such as vinyl, allyl, octenyl, decenyl, dodecenyl, cyclohexenyl and the like. The term "lower alkenyl" intends an alkenyl group of two to six carbon atoms, and specifically includes vinyl and allyl. The term "cycloalkenyl" refers to cyclic alkenyl groups.

The term "alkynyl" denotes a branched or unbranched hydrocarbon group of 2 to 18, or 2 to 12 in some embodiments, carbon atoms containing at least one triple bond, such as acetylenyl, n-propynyl, n-butynyl, isobutynyl, octynyl, decynyl and the like. The term "lower alkynyl" intends an alkynyl group of two to six carbon atoms, and includes, for example, acetylenyl and propynyl. The term "cycloalkynyl" refers to cyclic alkynyl groups.

The term "hydroxyl", alone or in combination with other groups, refers to —OH.

The term "aryl", alone or in combination with other groups, refers to an aromatic carbocyclic group comprising 6 to 14, preferably 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. Preferred "aryl" is phenyl.

The phrase "aryl substituted by", alone or in combination with other groups, refers to an aryl which is substituted by one or multiple substituents, preferably 1-4 substituents, whereby substitution at each ring atom individually is possible, with a substituent individually selected from the group as specified for each specific "aryl substituted by", e.g. from halogen, cyano, halogen-lower alkoxy, halogen-lower alkyl, lower alkoxy, and lower alkyl. Examples are halogen-aryl, chlorophenyl. fluoro-phenyl, lower alkyl-aryl, methyl-phenyl, lower alkoxy-aryl, methoxy-phenyl and the like.

The term "heteroaryl", alone or in combination with other groups, refers to an aromatic carbocyclic group of having a single 4 to 8 membered ring or multiple condensed rings comprising 6 to 14, more preferably 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, benzooxazinyl, benzo thiazinyl, benzo thiazolyl, benzo thienyl, benzo triazolyl, furyl, imidazolyl, indazolyl, indolyl, isoquinolinyl, isothiazolyl, isoxazolyl, oxazolyl, pyrazinyl, pyrazolyl (pyrazyl), pyrazolo[1,5-a]pyridinyl, pyridazinyl, pyridinyl, pyrimidinyl, pyrrolyl, quinolinyl, tetrazolyl, thiazolyl, thienyl, triazolyl and the like. Preferred are 1H-pyrazolyl, furyl, isoxazolyl, oxazolyl, pyrazinyl, pyrazolyl, pyridazinyl, pyridinyl, pyridinyl-N-oxide and pyrimidinyl. More preferred heteroaryls are pyridinyl, pyrazolyl, pyrazinyl and pyrimidinyl. Most preferred are pyridin-2-yl, pyrazin-2-yl, 1H-pyrazol-3-yl and pyrimidin-2-yl.

The phrase "heteroaryl substituted by", alone or in combination with other groups, refers to a heteroaryl which is substituted by one or multiple substituents, preferably 1-4 substituents, whereby substitution at each ring atom individually is possible, the substituent is individually selected from the group as specified for each specific "heteroaryl substituted by", i.e. for example from cyano, halogen, halogen-lower alkoxy, halogen-lower alkyl, lower alkoxy, and lower alkyl. Preferred "heteroaryl substituted by" are heteroaryl substituted by 1-2 substituents individually selected from cyano, halogen, halogen-lower alkoxy, halogen-lower alkyl and lower alkyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

The compounds of the present invention can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

In the first aspect of the invention, there is provided a process for preparing dihydro-2H-pyran derivatives of formula I:

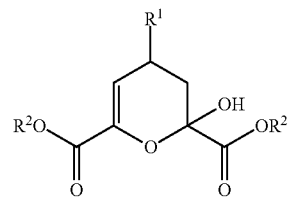

wherein $R^1$ is alkyl, cycloalkyl, aryl, heterocycloalkyl or heteroaryl, which is optionally substituted with one or more substituent selected from the group consisting of alkyl, alkenyl, alkynyl, alkoxy, nitro, cyano, halogen, hydroxyl, mono- or polyhalo alkyl, mono- or polyhalo alkoxy and phenyl; and $R^2$ is alkyl or benzyl;

which process comprises reacting aldehydes of the following formula:

wherein $R^1$ is as defined in the above;
with pyruvates of the following formula:

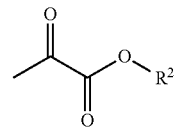

wherein $R^2$ is as defined in the above;
in the presence of catalytic amount of β-proline.

In one embodiment, the present invention relates to a compound of formula II:

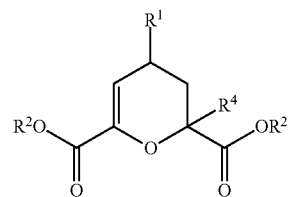

wherein $R^1$ and $R^2$ are as defined above, and $R^4$ is hydroxyl or halogen; or racemate, enantiomer, diastereomer, mixture thereof, or pharmaceutically acceptable salt thereof.

In a preferable embodiment of the compound of formula II above, $R^1$ is $C_1$-$C_{18}$-alkyl, $C_3$-$C_{18}$-cycloalkyl, phenyl, naphthyl or 5- or 6-membered heteroaryl containing at least one hetero atom selected from nitrogen, oxygen and sulfur, which is optionally substituted with one or more substituents selected from consisting of $C_1$-$C_{18}$-alkyl, $C_2$-$C_{18}$-alkenyl, $C_2$-$C_{18}$-alkynyl, $C_1$-$C_{18}$-alkoxy, nitro, cyano, halogen, hydroxyl, mono- or polyhalo-$C_1$-$C_{18}$-alkyl, mono- or polyhalo-$C_1$-$C_{18}$-alkoxy and phenyl; $R^2$ is $C_1$-$C_{18}$-alkyl or benzyl; and $R^4$ is hydroxyl or halogen.

Catalysts and reaction conditions are evaluated in the reaction of ethyl pyruvate and p-nitrobenzaldehyde to yield dihydro-2H-pyran derivative. Detailed conditions and results are shown in Example 1. The reaction in the presence of pyrrolidine in $CH_3CN$ gives the product in only trace yield (entry 6). Use of triethylamine, DBU, or DMAP as the catalyst does not afford the dihydro-2H-pyran derivative (entries 1-3). Reaction in the presence of pyrrolidine and acetic acid (1:1)

gives the dihydro-2H-pyran derivative in a moderate yield (entry 13). β-Proline may be the best catalyst among tested (entry 5). A solvent screen of the reaction using β-proline as catalyst shows that CH₃CN is a preferable solvent among tested (see Example 2). With further optimization, the reaction can be performed using various conditions, preferably using ethyl pyruvate (3.0 mmol), p-nitrobenzaldehyde (1.0 mmol), and β-proline (0.2 mmol) in CH₃CN at room temperature (25° C.) for 24 hours, thereby obtaining the dihydropyran derivative in at least 72% yield.

As a general procedure, the compound of formula I of the present invention can be obtained by the reaction of aldehyde and two equivalent of pyruvate in the presence of β-proline as a catalyst, in suitable solvent such as CH₃CN, at ambient temperature as shown in below scheme:

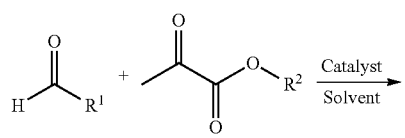

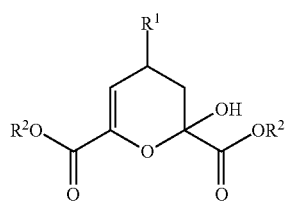

wherein $R^1$ and $R^2$ are as defined above.

Aldehyde used in the present invention is either commercially available or easily prepared according to method and starting material well known in the art. Pyruvate used in the present invention is either commercially available or easily prepared by the reaction of pyruvate and corresponding alcohol. Pyruvate should be used in an amount of two or more equivalent, preferably in the range of 2.1 to 3 equivalents based on aldehyde. β-Proline as a catalyst can be used in an amount of 5 to 50 mol %, preferably 10 to 25 mol % based on aldehyde. Both (S)- and (R)-enantiomer and racemate of β-proline can be used as a catalyst.

The reaction can be carried out in a solvent, preferably acetonitrile in the view of conversion. Reaction temperature is from ambient temperature to boiling point of solvent. In order to obtain the object product selectively, in mild condition, in particular ambient temperature is preferred. The reaction time is more than one hour, preferably in the range of 24 to 48 hours.

By well known purification technique, such as extract, concentration and column chromatography, the object compound can be obtained in sufficient purity. According to the process of the present invention, for example, following compound can be prepared:

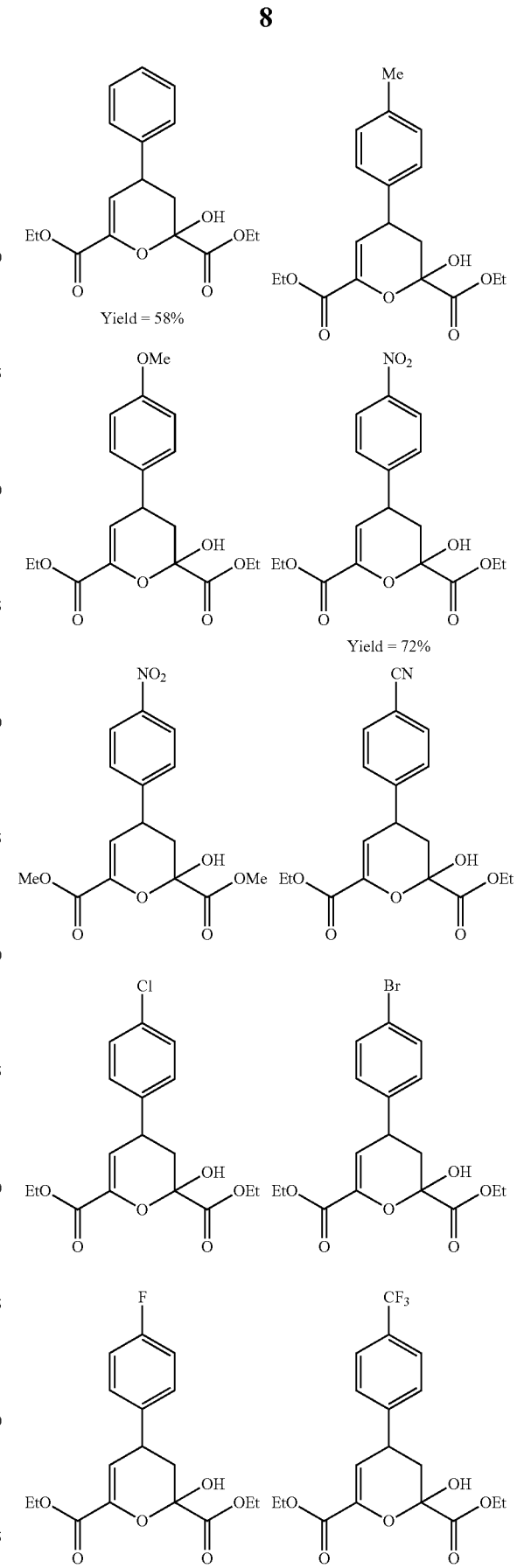

-continued

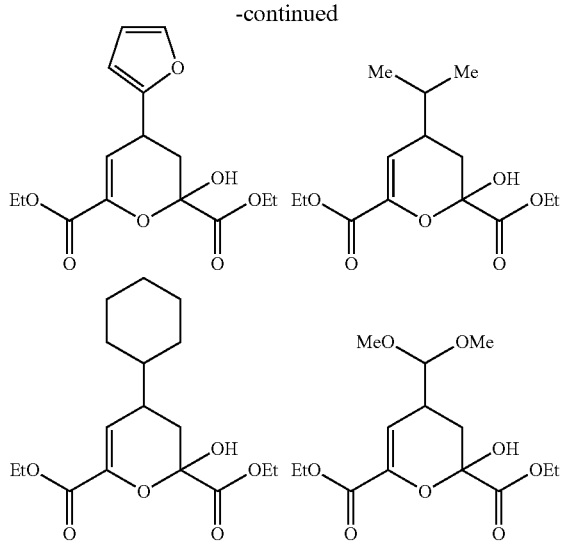

Dihydropyran derivatives of formula I obtained by the cascade reactions were used for further transformations. Thus, in a second aspect of the present invention, there is provided a process for preparing cyclohexane derivatives of formula III:

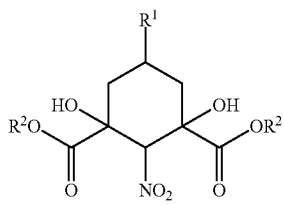

III wherein $R^1$ and $R^2$ are as defined above;
which process comprises reacting the dihydro-2H-pyran derivatives of formula I above with nitromethane in the presence of base.

In a preferable embodiment, the base is (−)-cinchonidine, DMAP, or triethylamine. In case a diastereomeric dihydro-2H-pyran derivative is used, the isolated cyclohexane product is also a single diastereomer.

In one embodiment, the present invention relates to a compound of formula IV or racemate, enantiomer, diastereomer, mixture thereof, or pharmaceutically acceptable salt thereof:

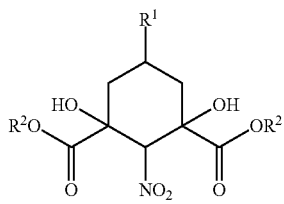

IV wherein $R^1$ and $R^2$ are as defined above; and $R^4$ is hydroxyl or halogen.

In a preferable embodiment, $R^1$ is $C_1$-$C_{18}$-alkyl, $C_3$-$C_{18}$-cycloalkyl, phenyl, naphthyl or 5- or 6-membered heteroaryl containing at least one hetero atom selected from nitrogen, oxygen and sulfur, which is optionally substituted with one or more substituents selected from consisting of $C_1$-$C_{18}$-alkyl, $C_2$-$C_{18}$-alkenyl, $C_2$-$C_{18}$-alkynyl, $C_1$-$C_{18}$-alkoxy nitro, cyano, halogen, hydroxyl, mono- or polyhalo-$C_1$-$C_{18}$-alkyl, mono- or polyhalo-$C_1$-$C_{18}$-alkoxy and phenyl.

In another preferable embodiment, $R^2$ is $C_1$-$C_{18}$-alkyl or benzyl.

Further, the following cyclohexane derivative can be debenzylated to diacid as shown in below scheme:

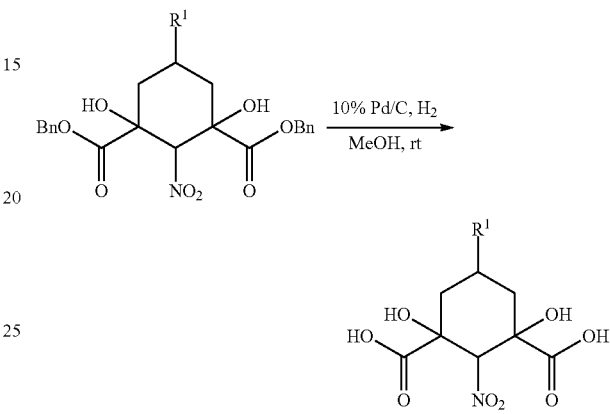

Reduction of the nitro group of the cyclohexane derivative may give corresponding amine as shown in below scheme: The highly functionalized amino acid derivative was easily accessed in a short route using the cascade reaction.

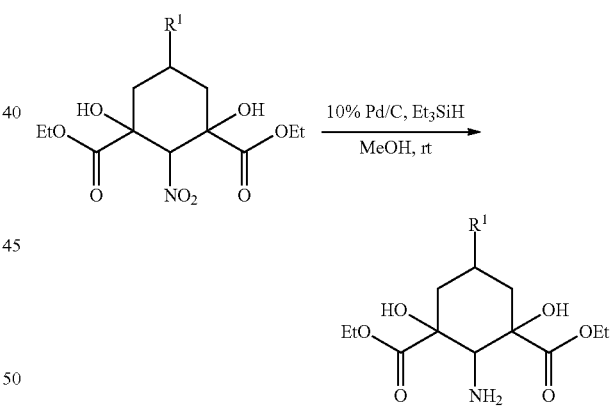

Reactions of dihydropyran derivatives of formula I with N,N-diethylaminosulfur trifluoride (DAST) will afford fluorinated products as shown below. Fluoropyran derivatives are often inhibitors and biofunctional molecules.

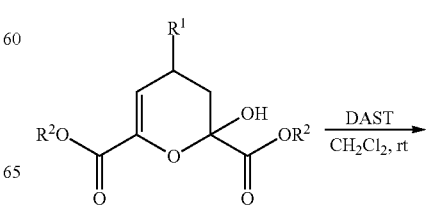

-continued

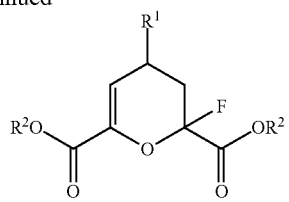

In a still other embodiment of the present invention, there is provided a process for preparing dihydropyran derivatives of formula V:

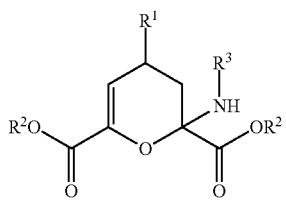

wherein $R^1$ and $R^2$ are as defined above; and $R^3$ is alkyl, cycloalkyl, aryl or heteroaryl, which is optionally substituted with one or more substituents selected from the group consisting of alkyl, alkenyl, alkynyl, alkoxy, nitro, cyano, halogen, hydroxyl, mono- or polyhalo alkyl, mono- or polyhalo alkoxy and phenyl;
which process comprises reacting the dihydro-2H-pyran derivatives of formula I with amines of the following formula:

$R^3$—$NH_2$ wherein $R^3$ is as defined in the above.

In yet another embodiment, the present invention relates to a compound of formula V or a racemate, enantiomer, diastereomer, mixture thereof, or pharmaceutically acceptable salt thereof:

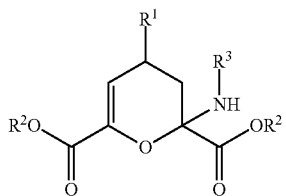

wherein $R^1$ to $R^3$ are as defined above.

In a preferable embodiment, $R^1$ is $C_1$-$C_{18}$-alkyl, $C_3$-$C_{18}$-cycloalkyl, phenyl, naphthyl or 5- or 6-membered heteroaryl containing at least one hetero atom selected from nitrogen, oxygen and sulfur, which is optionally substituted with one or more substituents selected from consisting of $C_1$-$C_{18}$-alkyl, $C_2$-$C_{18}$-alkenyl, $C_2$-$C_{18}$-alkynyl, $C_1$-$C_{18}$-alkoxy, nitro, cyano, halogen, mono- or polyhalo-$C_1$-$C_{18}$-alkyl, mono- or polyhalo-$C_1$-$C_{18}$-alkoxy and phenyl.

In another preferable embodiment, $R^2$ is $C_1$-$C_{18}$-alkyl or benzyl.

In a further preferable embodiment, $R^3$ is $C_1$-$C_{18}$-alkyl, $C_3$-$C_{18}$-cycloalkyl, phenyl, naphthyl or 5- or 6-membered heteroaryl containing at least one hetero atom selected from nitrogen, oxygen and sulfur, which is optionally substituted with one or more substituents selected from consisting of $C_1$-$C_{18}$-alkyl, $C_2$-$C_{18}$-alkenyl, $C_2$-$C_{18}$-alkynyl, $C_1$-$C_{18}$-alkoxy, nitro, cyano, halogen, mono- or polyhalo-$C_1$-$C_{18}$-alkyl, mono- or polyhalo-$C_1$-$C_{18}$-alkoxy and phenyl.

As described above, various amines can be used to react with the dihydro-2H-pyran derivatives of formula I for preparing compounds of formula V. In addition, when hydrazine or 1,2-diaminobenzene are used for reacting with the dihydro-2H-pyran derivatives of formula I, the following compounds can be obtained:

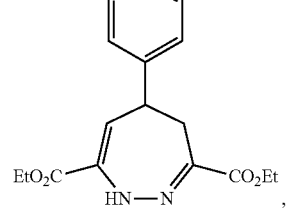

,

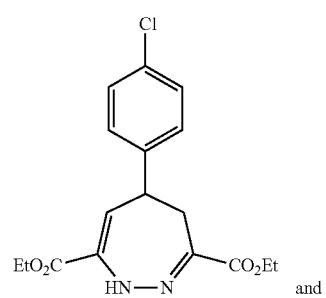

and

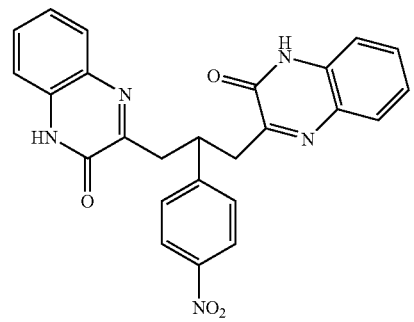

Particular examples of a compound of the present invention is selected from the group consisting of:

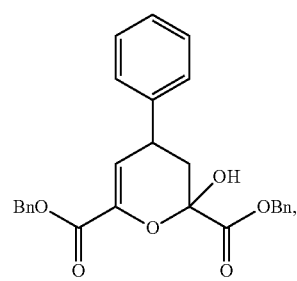

-continued
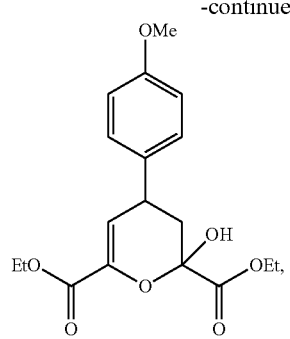
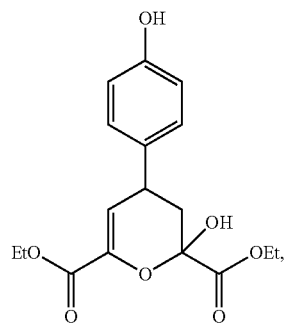
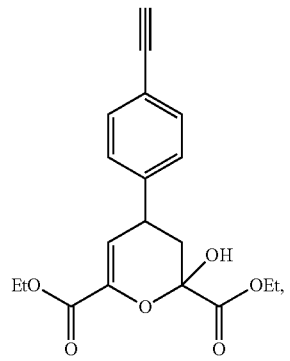
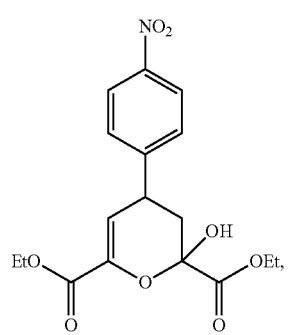
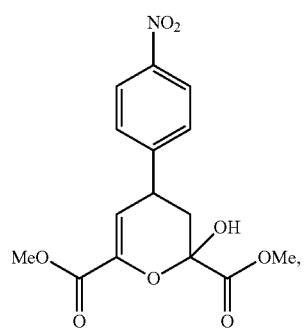
-continued
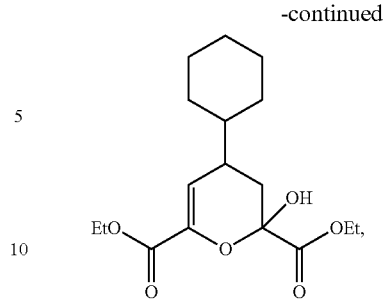
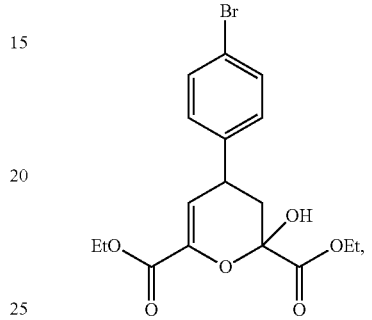

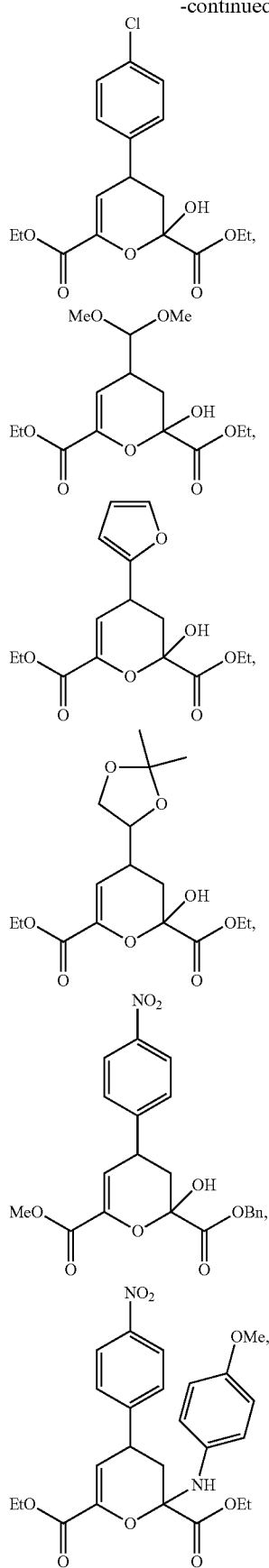
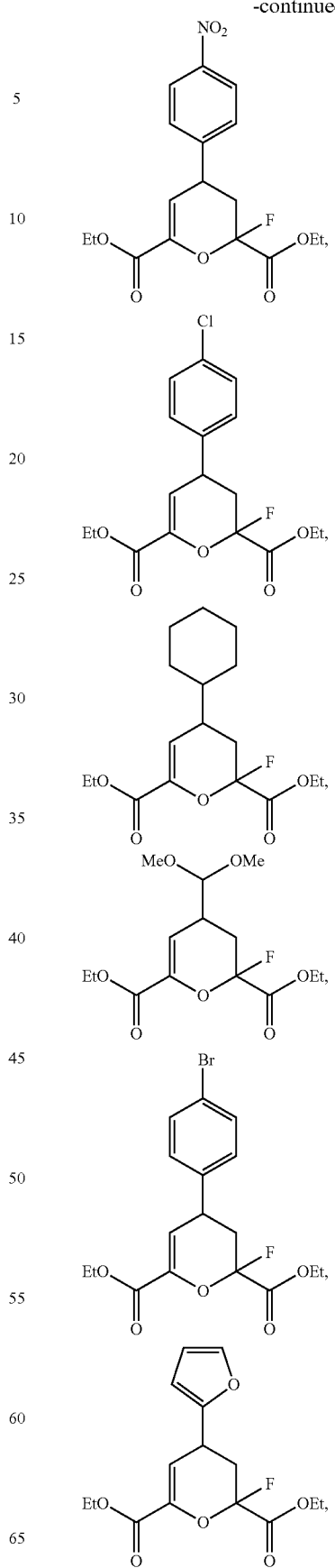

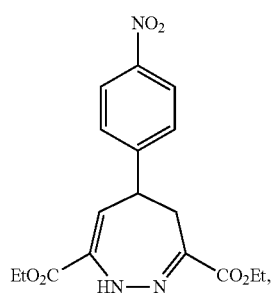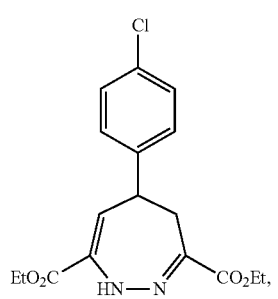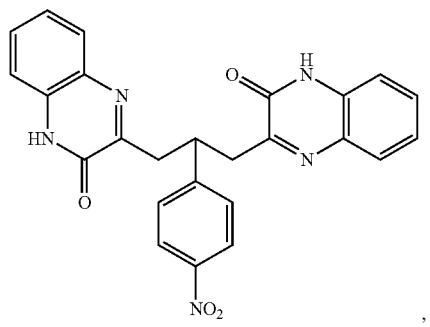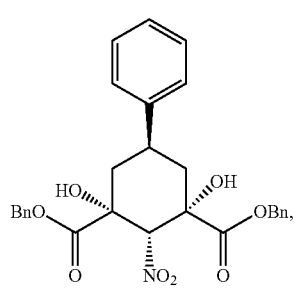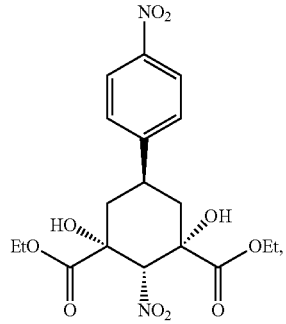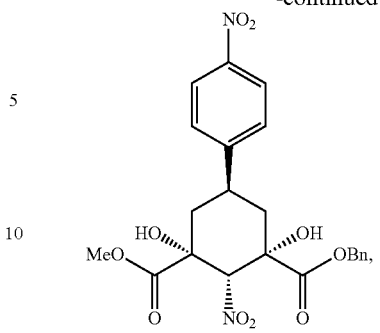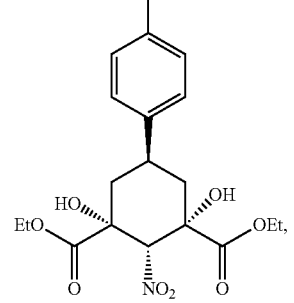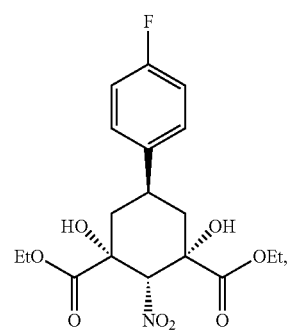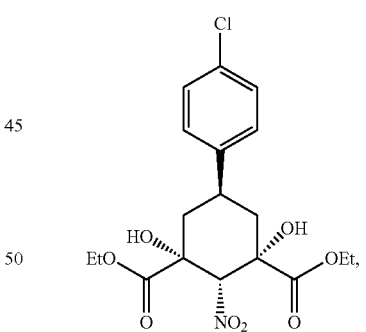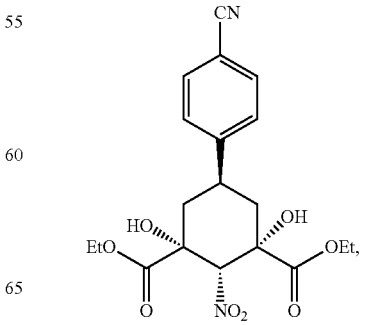

-continued

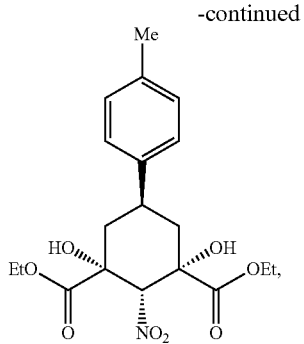
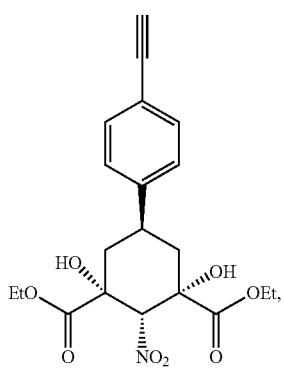
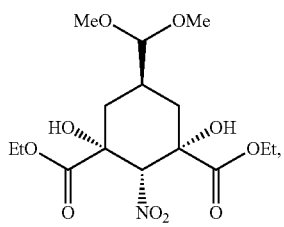
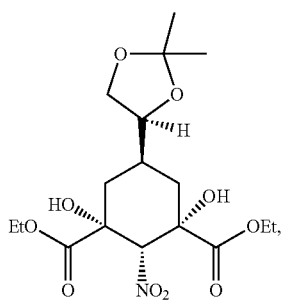
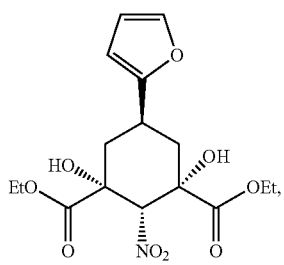

-continued

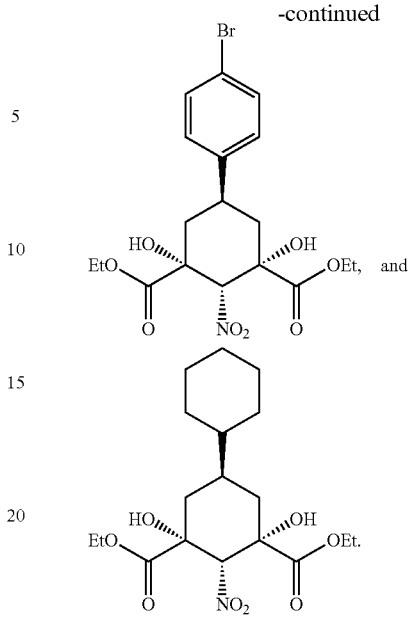

Pharmacological Tests

The compounds of formula II, IV and V and their pharmaceutically acceptable salts possess valuable pharmacological properties. It has been found that the compounds of the present invention are associated with anti-cancer activity. The compounds were investigated in accordance with the test given hereinafter.

Cytotoxicity:

K562 cells (American Type Culture Collection) were cultured in a culture medium containing 10% (v/v) fetal calf serum (FCS) (manufactures by Sigma) to logarithmic phase. The cells were seeded in 96-well microtiter plate at a density of 5000 cells/well in 100 µL cell culture medium and incubated at 37° C. and 5% $CO_2$ in a humidified incubator overnight. The test compounds of various concentrations were added in a well at 10 fold concentration in 1/10 volume of medium without FCS. After 6-48 hrs incubation at 37° C. in the $CO_2$ incubator, 10 µL solution of the viable cell counting reagent, Cell counting Kit-8 (5 mmol/L WST-8, 0.2 mmol/L 1-Methoxy PMS, 150 mmol/L NaCl) (manufactured by Dojindo) was added to each well, and reacted for 1 to 4 hours in the $CO_2$ incubator. After the incubation, an absorbance of formazan, generated by reduction of WST-8 was determined at 450 nm using a microplate reader.

The assay readout is correlated with the viable cell numbers. Small values correspond to high inhibition and larger values to low inhibition of the cell growth. To determine $IC_{50}$ values (i.e. the concentration inhibiting the cell growth by 50%) of the compounds of formula II, IV and V, several assays were made with a range of concentrations chosen empirically to give low, high and intermediate inhibition of the growth and determined using the curve fitting software.

The exemplified compounds according to formula II, IV and V have an inhibitory activity in this assays ($IC_{50}$) particular less than 1000 µM, more particular less than 100 µM. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed.

The results are shown in Table 1.
TABLE 1
| Structure | Cytotoxicity K562 IC$_{50}$ (μM) |
|---|---|
| 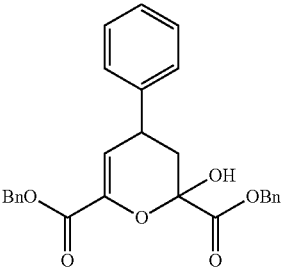 [SMILES: O=C(OCc1ccccc1)C1=CC(c2ccccc2)CC(O)(C(=O)OCc2ccccc2)O1] | 149 μM |
| 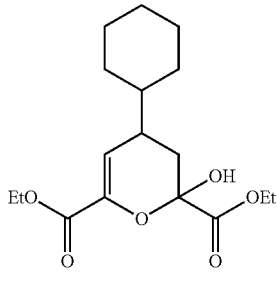 [SMILES: CCOC(=O)C1=CC(C2CCCCC2)CC(O)(C(=O)OCC)O1] | 58 μM |
| 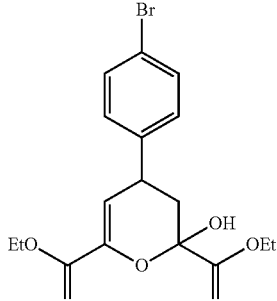 | 80 μM |
| 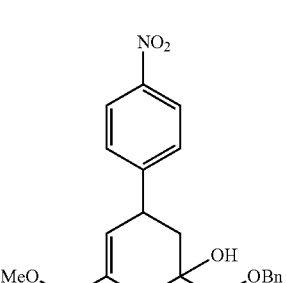 | 81 μM |
TABLE 1-continued
| Structure | Cytotoxicity K562 IC$_{50}$ (μM) |
|---|---|
| 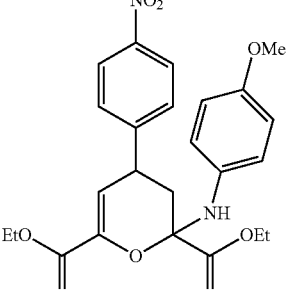 | 12 μM |
| 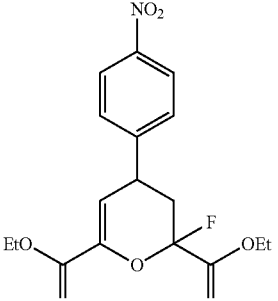 | 11 μM |
| 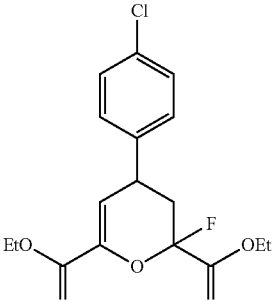 | 52 μM |
| 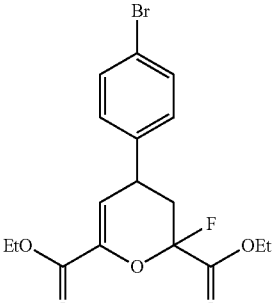 | 53 μM |
| 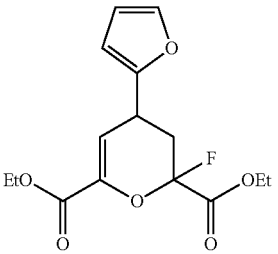 | 135 μM |

TABLE 1-continued

| Structure | Cytotoxicity K562 IC$_{50}$ (μM) |
|---|---|
| (4-nitrophenyl dihydrodiazepine with EtO$_2$C and CO$_2$Et groups) | 148 μM |
| (phenyl-substituted cyclohexane with HO, OH, BnO$_2$C, CO$_2$Bn, NO$_2$) | 54 μM |
| (4-nitrophenyl cyclohexane with HO, OH, MeO$_2$C, CO$_2$Bn, NO$_2$) | 90 μM |
| (4-CF$_3$-phenyl cyclohexane with HO, OH, EtO$_2$C, CO$_2$Et, NO$_2$) | 144 μM |
| (4-Br-phenyl cyclohexane with HO, OH, EtO$_2$C, CO$_2$Et, NO$_2$) | 144 μM |
| (cyclohexyl-substituted cyclohexane with HO, OH, EtO$_2$C, CO$_2$Et, NO$_2$) | 105 μM |

Pharmaceutical Compositions

The compounds of formula II, IV and V as well as their pharmaceutical acceptable salts can be used as medicaments, e.g. in the form of pharmaceutical preparations. The pharmaceutical preparations can be administered orally, e.g. in the form of tablets, coated tablets, dragees, hard and soft capsules, solutions, emulsions or suspensions. The administration can however, also be effected rectally, e.g. in the form of suppositories, or parenterally, e.g. in the form of injection solutions.

The compounds of formula II, IV and V and their pharmaceutical acceptable salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragees and hard gelatine capsules.

Suitable excipients for soft gelatine capsules are e.g. vegetable oils, waxes, fats, semisolid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can be vary within wide limits and will, of course, be fitted to the individual requirements in each particular case. In general, in the case of oral administration a daily dosage of about 10 to 1000 mg per person of a compound of general formula II, IV and V should be appropriate, although the above upper limit can be exceeded when necessary.

EXAMPLES

The invention is illustrated hereinafter by Examples, which have no limiting character. In case the preparative examples are obtained as a mixture of enantiomers and diastereomers, the pure enantiomers or diastereomers can be separated by methods described herein or by methods known to the person skilled in the art, such as e. g. chiral chromatography or crystallization.

Example 1

Screening of Catalysts

In the following example, the effect of the added catalyst was assayed to illustrate the effect of various catalysts on the overall percent yield of the reaction. To a solution of aldehyde (1.0 mmol) and ethyl pyravate (348 mg, 3.0 mmol) in $CH_3CN$ (1 mL) was added the selected catalysts (10 mol %) and the mixture was stirred at 25° C. for 24 h or 48 h. The mixture was poured into aqueous saturated $NH_4Cl$ solution and extracted with ethyl acetate. The organic layers were combined, dried over $Na_2SO_4$, filtered, concentrated, and purified by flash column chromatography (hexane/EtOAc=7:3) to afford the 4-substituted dihydropyran derivative. The overall reaction scheme and the experimental results are illustrated below:

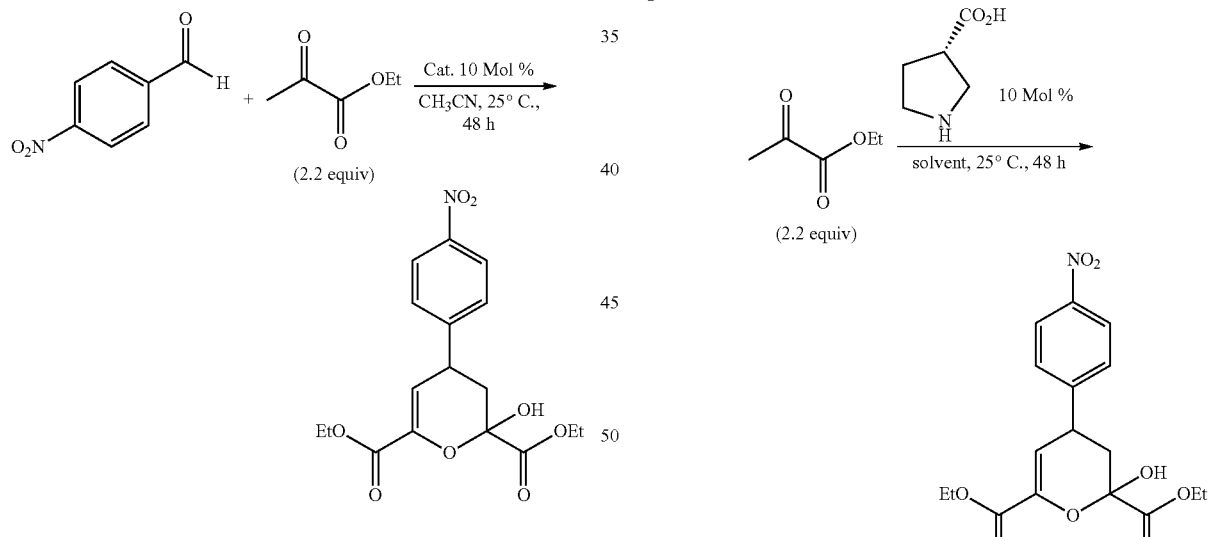

| Entry | Catalyst (10 mol %) | Yield (%)[a] |
|---|---|---|
| 1 | $Et_3N$ | 0 |
| 2 | DBU | 0 |
| 3 | DMAP | 0 |
| 4 | β-Alanine | 0 |
| 5 | (S)-β-Proline | 49 |
| 6 | Pyrrolidine | 4 |
| 7 | 3-(Trifluoromethanesulfonylamino)pyrrolidine | 9 |
| 8 | L-Histidine | 0 |
| 9 | L-Tryptophan | 0 |
| 10 | L-Valine | 0 |
| 11 | O-t-Butyl threonine | 0 |
| 12 | (S)-β-Proline (10 mol %) + $Et_3N$ (10 mol %) | 0 |
| 13 | Pyrrolidine (10 mol %) + $CH_3COOH$ (15 mol %) | 27 |

Reaction was conducted on the aldehyde 1 mmol scale in 1 mL solvent at r.t. for 48 h.
[a]Isolated product yield after column chromatography.

Example 2

Screening of Reaction Conditions

In the following example, the reaction conditions were assayed to determine the affects of reaction conditions on overall percent yield. To a solution of aldehyde (1.0 mmol) and ethyl pyravate (348 mg, 3.0 mmol) in a selected solvent (1 mL) was added (−)-β-proline (10 mol %) and the mixture was stirred at 25° C. for 48 h. The mixture was poured into aqueous saturated $NH_4Cl$ solution and extracted with ethyl acetate. The organic layers were combined, dried over $Na_2SO_4$, filtered, concentrated, and purified by flash column chromatography (hexane/EtOAc=7:3) to afford the 4-substituted dihydropyran derivative. The overall reaction scheme and tabulated experimental results are illustrated below.

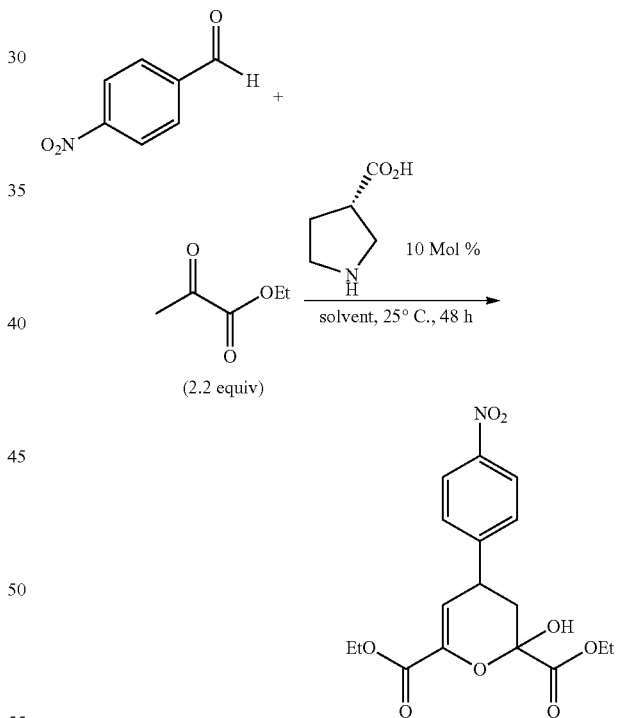

| Entry | Solvent | Yield (%)[a] |
|---|---|---|
| 1 | Toluene | 6 |
| 2 | i-PrOH | 11 |
| 3 | DMF | 15 |
| 4 | 1,4-Dioxane | 6 |
| 5 | DMSO | Not clean (formation of many byproducts) |
| 6 | THF | 7[b] |
| 7 | $CH_2Cl_2$ | 5[b] |

27
-continued

| Entry | Solvent | Yield (%)[a] |
|---|---|---|
| 8 | CHCl$_3$ | 5[b] |
| 9 | CH$_3$CN | 19[b,c] |
| 10 | CH$_3$CN | 25[b] |
| 10 | CH$_3$CN | 49 |
| 10 | CH$_3$CN | 72[d] |
| 11 | CH$_3$CN/H$_2$O (3:1) | 0 |

Reaction was conducted on the aldehyde 1 mmol scale in 1 mL solvent 1 mL at r.t. for 48 h.
[a]Isolated product yield after column chromatography.
[b]Catalyst 5 mol % was used.
[c]Pyruvate 1 equiv was used.
[d]Catalyst 20 mol % and pyruvate 3 equiv were used.

Example 3

Synthesis of Cyclohexane Derivatives

The reaction product of Example 1 was further reacted in a second reaction step in order to prepare the corresponding cyclohexane derivative. To a solution of the dihydropyran (0.1 mmol) and nitromethane (1.0 mmol) in CH$_2$Cl$_2$ (0.5 mL) was added (−)-cinchonidine (0.015 mmol) and the mixture was stirred at 25° C. for 15 h. The mixture was poured into aqueous saturated NH$_4$Cl solution and extracted with CH$_2$Cl$_2$. The organic layers were combined, dried over Na$_2$SO$_4$, filtered, concentrated, and purified by flash column chromatography (hexane/EtOAc=7:3) to afford the cyclohexane derivative. Reaction using DMAP (0.1 mmol) or triethylamine (0.015 mmol) instead of (−)-cinchonidine also afforded the same product. The overall reaction scheme is illustrated as follows:

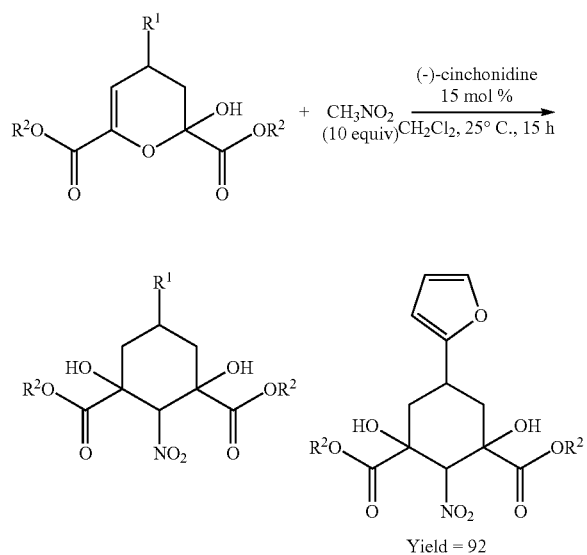

28
-continued

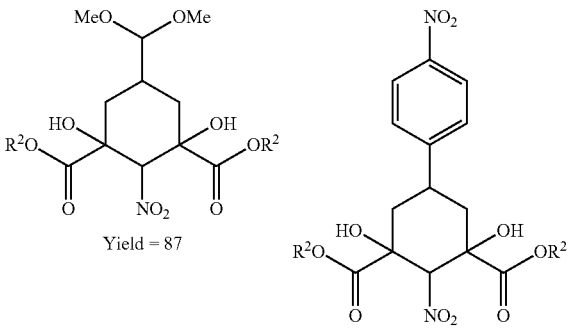

Yield = 87

Yield = 81% (76%)[a]
[a]DMAP (1 equiv) used

R$^1$ = aryl, alkyl, hetreoaryl
R$^2$ = ethyl,

Example 4

Synthesis of Amino Substituted Dihydropyran Derivatives

The reaction product of Example 1 was further reacted in a second reaction step in order to prepare the corresponding amino substituted dihydropyran derivatives. To a solution of 4-substituted dihydropyran (0.05 mmol) in CH$_2$Cl$_2$ (0.5, mL) was added amine (0.75 mmol) and the mixture was stirred at 25° C. for 24 h. The mixture was poured into aqueous saturated NH$_4$Cl solution and extracted with CH$_2$Cl$_2$. The organic layers were combined, dried over Na$_2$SO$_4$, filtered, concentrated, and purified by flash column chromatography (hexane/EtOAc=7:3) to afford the amino substituted dihydropyran derivative. The overall reaction scheme is illustrated as follows:

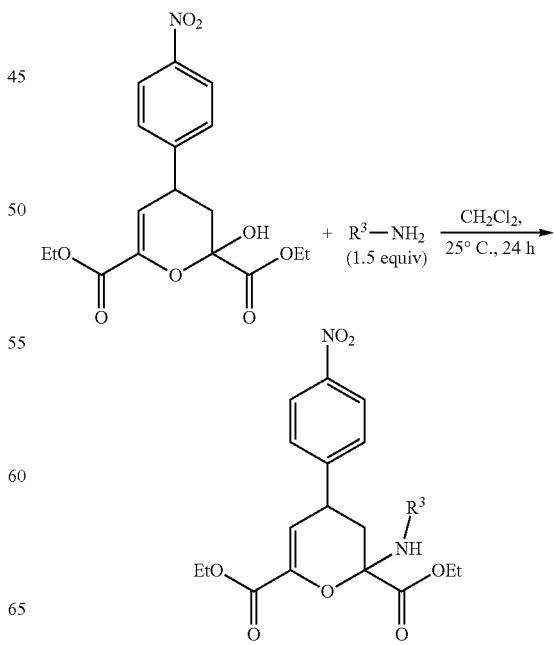

-continued

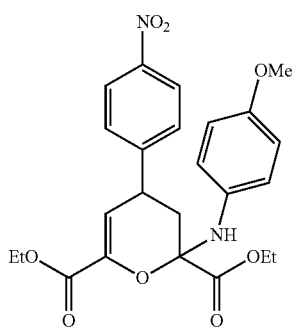 [SMILES: CCOC(=O)C1=CC(c2ccc([N+](=O)[O-])cc2)CC(Nc2ccc(OC)cc2)(C(=O)OCC)O1]

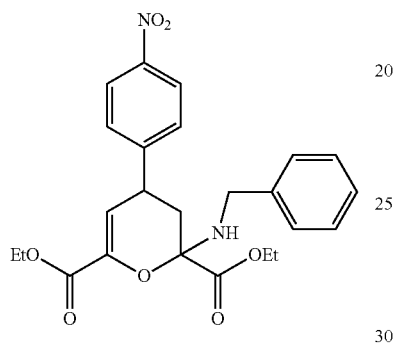

$R^3$ = aryl, alkyl,

The invention claimed is:

1. A compound of formula II:

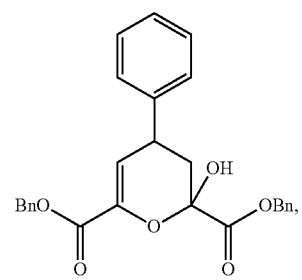

II wherein

R1 is alkyl, cycloalkyl, aryl, heterocycloalkyl or heteroaryl, which is optionally substituted with one or more substituent selected from the group consisting of alkyl, alkenyl, alkynyl, alkoxy, nitro, cyano, halogen, hydroxyl, mono- or polyhalo alkyl, mono- or polyhalo alkoxy and phenyl;

R2 is alkyl or benzyl; and $R^4$ is hydroxyl or halogen;

or racemate, enantiomer, diastereomer, mixture thereof, or pharmaceutically acceptable salt thereof.

2. The compounds of formula II according to claim 1, wherein $R^1$ is $C_1$-$C_{18}$-alkyl, $C_3$-$C_{18}$-cycloalkyl, phenyl, naphthyl or 5- or 6-membered heteroaryl containing at least one hetero atom selected from nitrogen, oxygen and sulfur, which is optionally substituted with one or more substituents selected from the group consisting of $C_1$-$C_{18}$-alkyl, $C_2$-$C_{18}$-alkenyl, $C_2$-$C_{18}$-alkynyl, $C_1$-$C_{18}$-alkoxy nitro, cyano, halogen, hydroxyl, mono- or polyhalo-$C_1$-$C_{18}$-alkyl, mono- or polyhalo-$C_1$-$C_{18}$-alkoxy and phenyl;

$R^2$ is $C_1$-$C_{18}$-alkyl or benzyl; and $R^4$ is hydroxyl or halogen;

or racemate, enantiomer, diastereomer, mixture thereof, or pharmaceutically acceptable salt thereof.

3. A pharmaceutical composition comprising a compound according to claim 1, and a pharmaceutically acceptable adjuvant.

4. A compound of formula II according to claim 1, selected from the group consisting of:

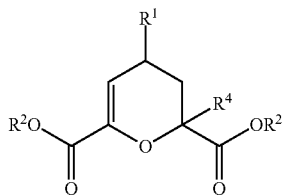

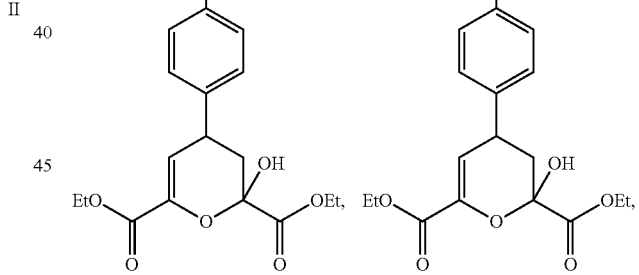

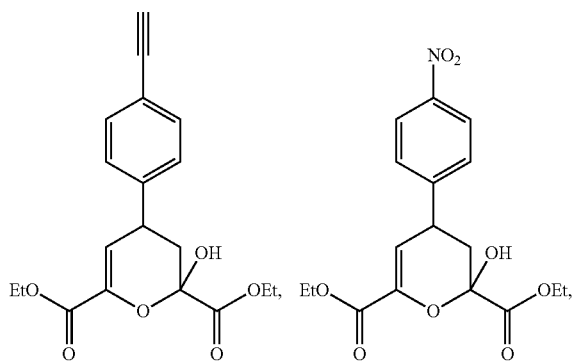

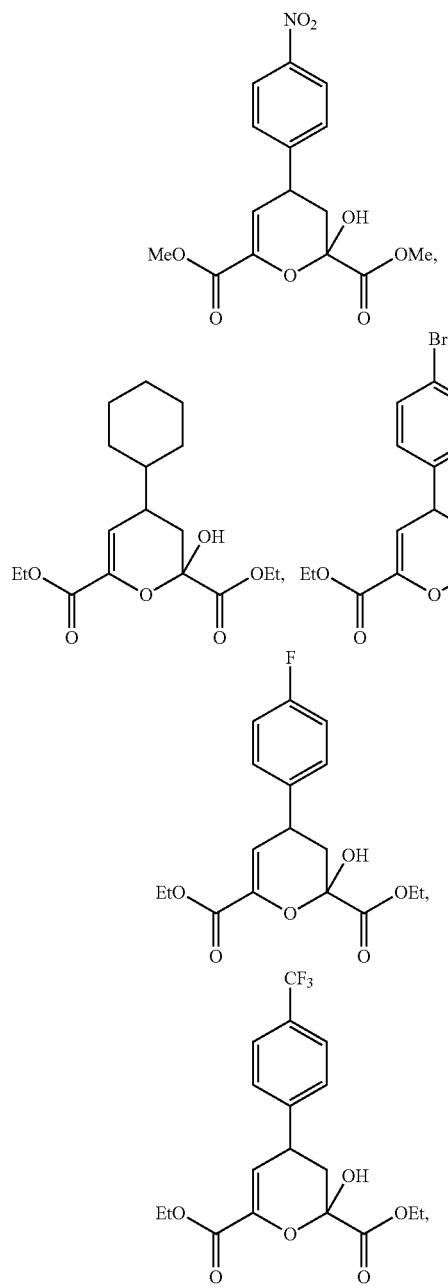
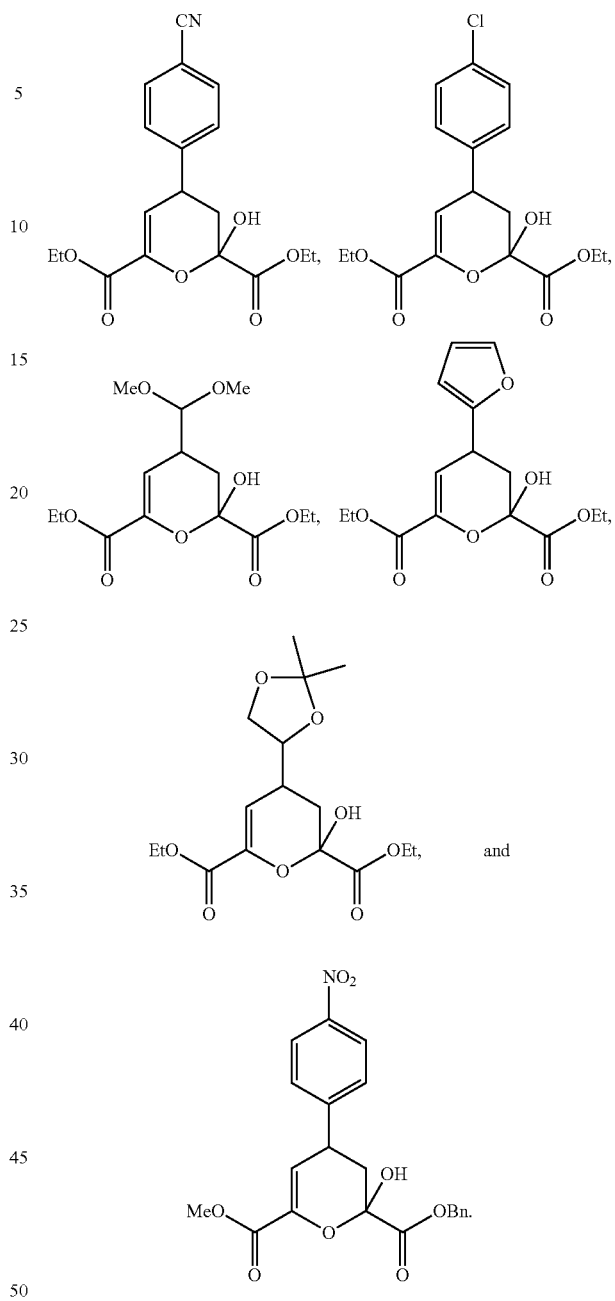
* * * * *